United States Patent [19]

Lee

[11] 4,284,777

[45] Aug. 18, 1981

[54] ANTIBACTERIALS: 1-DIFLUOROMETHYL-6,7-METHYLENE-DIOXY-1,4-DIHYDRO-4-OXO-3-QUINOLINECARBOXYLIC ACID AND ITS ESTERS

[75] Inventor: Kyu T. Lee, Wilmington, Del.

[73] Assignee: E. I. Du Pont de Nemours and Company, Wilmington, Del.

[21] Appl. No.: 121,487

[22] Filed: Feb. 14, 1980

Related U.S. Application Data

[60] Division of Ser. No. 972,959, Dec. 26, 1978, Pat. No. 4,216,324, which is a division of Ser. No. 758,331, Jan. 14, 1977, Pat. No. 4,147,788, which is a continuation-in-part of Ser. No. 660,852, Feb. 23, 1976, abandoned.

[51] Int. Cl.$^3$ .................................................. C07D 491/14
[52] U.S. Cl. ........................................ 546/90; 424/258
[58] Field of Search ............................................ 546/90

[56] References Cited

U.S. PATENT DOCUMENTS

| 3,149,104 | 9/1964 | Lesher et al. | 546/123 |
| 3,287,458 | 11/1966 | Kaminsky et al. | 546/90 |
| 3,509,257 | 4/1970 | Kaminsky et al. | 424/258 |
| 3,524,858 | 8/1970 | Kaminsky et al. | 546/90 |
| 3,591,697 | 7/1971 | Kaminsky et al. | 424/258 |
| 3,753,993 | 8/1973 | Lesher et al. | 546/156 |
| 3,761,482 | 9/1973 | Nakagome et al. | 546/90 |
| 3,907,808 | 9/1975 | Lesher et al. | 546/156 |
| 3,917,605 | 11/1975 | Nakagome et al. | 546/90 |
| 3,927,000 | 12/1975 | Bailey | 546/139 |
| 4,036,962 | 7/1977 | Lee | 546/90 |
| 4,117,136 | 9/1978 | Hisada et al. | 546/156 |

FOREIGN PATENT DOCUMENTS

| 1076828 | 7/1967 | United Kingdom | 546/90 |
| 1240316 | 12/1967 | United Kingdom | 546/90 |
| 1337377 | 11/1973 | United Kingdom | 546/90 |
| 1398066 | 6/1975 | United Kingdom | 546/156 |

OTHER PUBLICATIONS

Fieser & Fieser, Reagents for Organic Synthesis, vol. I, p. 1058, Wiley Pub., (1967).
Hine et al., Journal of the American Chemical Society, vol. 79, pp. 5493–5494, (1957).
Banus et al., Journal of the Chemical Society, London, Part I, pp. 60–62, (1951).
Merck Index, 8th Edition, pp. 825 & 925, (1968).

*Primary Examiner*—Alan L. Rotman

[57] ABSTRACT

1-Difluoromethyl-6,7-methylenedioxy-1,4-dihydro-4-oxo-3-quinolinecarboxylic acid and certain of its alkyl-aminoalkyl esters, useful in treating bacterial infections in mammals.

3 Claims, No Drawings

ANTIBACTERIALS: 1-DIFLUOROMETHYL-6,7-METHYLENEDIOXY-1,4-DIHYDRO-4-OXO-3-QUINOLINECARBOXYLIC ACID AND ITS ESTERS

CROSS-REFERENCE TO RELATED APPLICATIONS

This is a division, of application Ser. No. 972,959, filed Dec. 26, 1978, Pat. No. 4,216,324 which in turn is a division of application Ser. No. 758,331, filed on Jan. 14, 1977, Pat. No, 4,147,788 which in turn is a continuation-in-part of Application Ser. No. 660,852 filed Feb. 23, 1976 now abandoned.

BACKGROUND

This invention relates to quinoline derivative antibacterials.

Kaminsky, in U.S. Pat. No. 3,287,458, discloses antibacterial 6,7-methylenedioxy-1,4-dihydro-4-oxo-quinolinecarboxylic acids substituted in the 1 position with lower alkyl or a variety of other substituents. The compound where this substituent is ethyl is commonly known as oxolinic acid.

Oxolinic acid is a highly effective anti-bacterial agent, but a high incidence of undesirable side effects is reported. Cox, Claire E., *Delaware Medical Journal*, November 1970, p. 327. And Kershaw and Leight (*Journal of Antimicrobial Therapy* 1, 311–315, 1975) have indicated that because of toxicity, "it should not be used as a first-line drug in the therapy of urinary tract infections."

Another quinoline derivative which is now marketed for the treatment of urinary tract infections is nalidixic acid. It was originally shown to be effective for this use; however, further experience with nalidixic acid has suggested that its usefulness may be limited by its tendency to rapidly evoke bacterial resistance. Ronald, A. R. et al. *New England Journal of Medicine*, 275:1081–1088 (1966). Moreover, a relatively high incidence of side effects also occurs with nalidixic acid administration. Cox, p. 327.

The compounds of the present invention are also highly effective antibacterial agents; but, unlike the prior art compounds, they do not produce undesirable side effects:

In the general pharmacology screen oxolinic acid produced ataxia, anorexia, excitation, and irritability and nalidixic acid produced some ataxia, and anorexia; whereas the compounds of this invention produced none of these untoward effects. (Tables 3 and 4)

SUMMARY

According to this invention, there is provided compounds of formula I and their pharmaceutically suitable salts, processes for their manufacture, pharmaceutical compositions containing them, and methods of using them to treat bacterial infections in mammals.

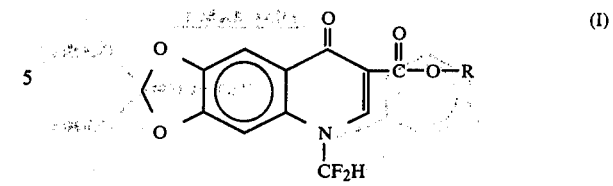

where
R = hydrogen or

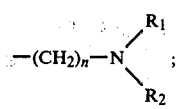

$R_1$ and $R_2$ independently = $C_1$–$C_3$ alkyl; and
n = 2 or 3.

DETAILED DESCRIPTION

Preferred Compounds

The compound most preferred because of its high level of antibacterial activity and absence of undesirable side effects is 1-difluoromethyl-6,7-methylenedioxy-1,4-dihydro-4-oxo-3-quinoline carboxylic acid.

Also preferred is 1-difluoromethyl-6,7-methylenedioxy-1,4-dihydro-4-oxo-3-quinolinecarboxylic acid, N,N-dietylaminoethyl ester.

Pharmaceutical Salts

Pharmaceutically suitable salts of the acid include those made with certain metals, such as sodium potassium and calcium, and also ammonium. The salts are prepared by adding an alcoholic or aqueous solution of MOH (where M is the metal) to a solution or suspension of the acid in a solvent, such as dimethylformamide, dimethylsulfoxide or ethanol. The salt product is isolated by filtration.

Pharmaceutically suitable acid addition salts of the esters include those made with physiologically acceptable acids that are known in the art; such salts include hydrochloride, sulfate, nitrate, phosphate, citrate, tartrate, maleate, and the like.

Synthesis

The ester starting materials for the process are prepared in the following manner (J. Med. Chem. 11, 160, 1968) which is schematically represented in diagram 1:

3,4-Methylenedioxyaniline (A), which is commercially available, is reacted with dialkyl alkoxymethylenemalonate (B) at 70°–100° C. with or without solvent (which is usually ethanol) to form a compound of formula C. C is converted to the ester starting material (C) by heating in Dowtherm A (a mixture of diphenyl ether and diphenyl) at 250°–255° C.

DIAGRAM 1

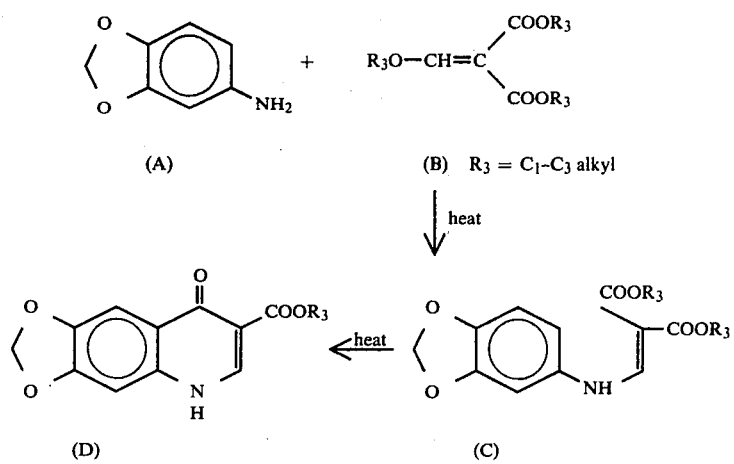

The compounds of this invention are prepared in the following manner, which is schematically represented in diagram 2:

The difluoromethyl group (:CF$_2$) is added to the ester starting material (D) by reacting it with HCF$_2$Cl in the presence of a base such as R$_4$OM, where R$_4$ is an alkyl group, such as methyl, ethyl, or t-butyl and M is an alkaline metal such as sodium, potassium, or lithium. The solvent for this reaction can be R$_4$OH where R$_4$ is as previously defined, or another aprotic solvent such as dimethylformamide, dimethylsulfoxide or ethyleneglycol dimethylether. The reaction temperature can be about 50°–100° C.

The difluoromethyl group can also be added to the ester starting material by pyrolysis of an alkaline metal salt of chlorodifluoroacetic acid in an aprotic solvent, such as diethyleneglycol dimethyl ether or diethyl malonate at elevated temperature.

The resulting difluoromethyl compound (E) is hydrolyzed by heating at about 80°–110° C. in dilute hydrochloric acid for about 1 to 2 hours to give the acid (F).

This is converted into its acid chloride (G) using PCl$_5$. The esters (H) are made by reacting the acid chloride (G) with the appropriate amminoalcohol in an inert solvent, such as benzene or toluene.

In addition to the compounds of formula I, the intermediate alkyl esters (E) and acid chloride (G) are also novel compounds.

DIAGRAM 2

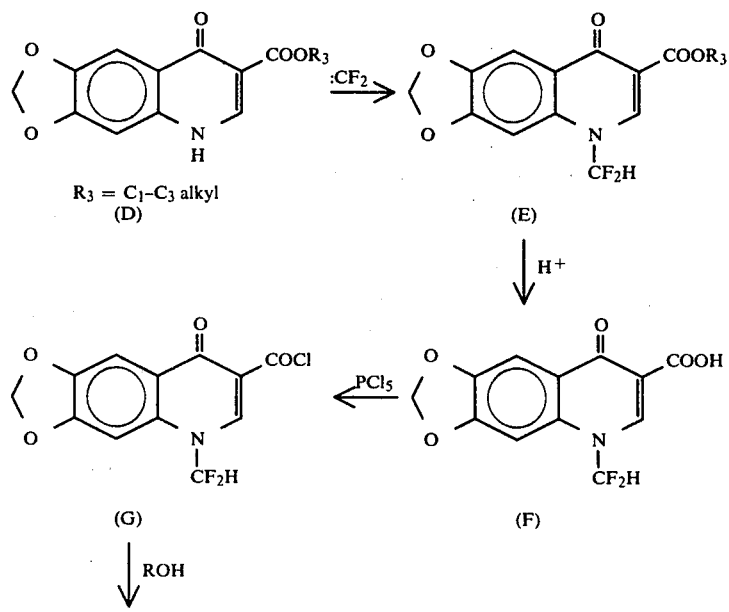

DIAGRAM 2

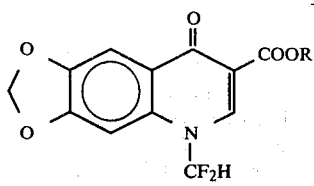

(H)

EXAMPLE 1

1-Difluoromethyl-6,7-methylenedioxy-1,4-dihydro-4-oxo-3-quinolinecarboxylic acid ethyl ester

Method A:

A mixture of 13 g of 6,7-methylenedioxy-1,4-dihydro-4-oxo-3-quinolinecarboxylic acid ethyl ester and 10.3 g of $NaOC_2H_5$ in 150 ml of ethanol is placed in a bomb, and 13.2 g of $HCF_2Cl$ added. The bomb is sealed and the temperature is raised to 80° C. and held there for 8 hours. The cooled mixture is poured into $H_2O$ and the solid precipitate is collected by filtration, dissolved in hot $CH_3CN$, and filtered while hot to remove the unreacted starting material. After cooling the filtrate, the solid product is isolated by filtration, m.p. 218°–219° C.

Method B

To a mixture of 10 g of 6,7-methylenedioxy-1,4-dihydro-4-oxo-3-quinolinecarboxylic acid ethyl ester in 50 ml of diethyleneglycol dimethyl ether (diglyme) is added, while maintaining the temperature at 160°–165° C., a solution of 13 g of sodium chlorodifluoroacetate dissolved in 50 ml of diglyme. After completion of the addition, the mixture is heated at 163° C. for an additional 0.5 hour, cooled, and poured into water. The solid precipitate is isolated by filtration and purified as in Method A, m.p. 219°–220° C. Its IR and NMR spectra are identical to those obtained from Method A.

Anal. Calc'd for $C_{14}H_{11}F_2NO_5$; C:54.03, H:3.56, N:4.50 Found: C:54.03, H:3.50, N:4.64.

EXAMPLE 2

1-Difluoromethyl-6,7-methylenedioxy-1,4-dihydro-4-oxo-3-quinolinecarboxylic acid A mixture of 27.5 g of 1-difluoromethyl-6,7-methylenedioxy-1,4-dihydro-4-oxo-3-quinolinecarboxylic acid, ethyl ester and 600 ml of 6 N hydrochloric acid is heated under reflux for 1.5 hours. The mixture is diluted with 1 liter of water, cooled, and filtered. The solid product is triturated with cold ethanol and filtered to give 24.5 g of the desired product, m.p. 327°–8° C. (dec). Anal. Calc'd for $C_{12}H_7F_2O_5$; C:50.89, H:2.49, N:4.95—Found; C:50.95, H:2.54, N:4.84.

EXAMPLE 3

1-Difluoromethyl-6,7-methylenedioxy-1,4-dihydro-4-oxo-3-quinolinecarboxylic acid, N,N-diethylaminoethyl ester A mixture of 5.0 g of 1-difluoromethyl-6,7-methylenedioxy-1,4-dihydro-4-oxo-3-quinolinecarboxylic acid and 4.2 g of $PCl_5$ in 170 ml of dry benzene is heated under reflux for 17 hours. The mixture is cooled and filtered to give the desired acid chloride.

The acid chloride is suspended on 100 ml of dry benzene and 20 g of 2-(N,N-diethylamino)ethanol is added. The resulting mixture is heated under reflux for 5 hours and concentrated under reduced pressure. Ice-water is added to the residue, and it is then made basic by adding aqueous NaOH. The solid precipitate is collected by filtration and recrystallized from $CH_3CN$, m.p. 164°–165° C. Anal. Calc'd for $C_{18}H_{20}F_2N_2O_5$; C:56.54, H:5.27, N:7.33—Found: C:56.54, H:5.30, N:7.37.

EXAMPLE 4

1-Difluoromethyl-6,7-methylenedioxy-1,4-dihydro-4-oxo-3-quinolinecarboxylic acid, 3-(N,N-dimethylamino)n-propyl ester The product can be obtained by substituting 3-(N,N-dimethylamino)-n-propanol for the 2-(N,N-dimethylamino)ethanol of Example 3.

Dosage Forms:

The antibacterial agents of this invention can be administered to exert their antibacterial activity by any means that produces contact of the active agent with the site of infection in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 5 to 100 milligrams per kilogram of body weight; and preferably 5 to 10 milligrams per kologram per day given in divided doses 2 to 4 times a day.

Dosage forms (compositions) suitable for internal administration contain from about 5 milligrams to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and, if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient. 200 milligrams of lactose, 30 milligrams of talc, and 10 milligrams magnesium stearate.

Capsules

A mixture of active ingredient in soybean oil is prepared and injected by means of a positive displacement pump into gelatin to form soft gelatin capsules containing 100 milligrams of the active ingredient. The capsules are washed in petroleum ether and dried.

Tablets

A large number of tablets are prepared by conventional procedures so that the dosage unit is 250 milligrams of active ingredient, 50 milligrams of ethyl cellulose, 5 milligrams of colloidal silicon dioxide, 5 milligrams of magnesium stearate, 10 milligrams of microcrystalline cellulose, 40 milligrams of cornstarch and 150 milligrams of lactose. Appropriate coatings may be applied to increase palatability or delay absorption.

Injectable

A parenteral composition suitable for adminstration by injection is prepared by stirring 5% by weight of active ingredient in 10% by volume propylene glycol and water. The solution is sterilized by filtration.

Suspension

An aqueous suspension is prepared for oral administration so that each 5 milliters contain 100 milligrams of finely divided active ingredient, 500 milligrams of acacia, 5 milligrams of sodium benzoate, 1.0 grams of sorbitol solution, U.S.P., 5 milligrams of sodium saccharin, and 0.025 milliliters of vanilla tincture.

Utility:

Use of the compounds of this invention as antibacterial agents in mammals is demonstrated by the following microbiological data for 1-difluoromethyl-6,7-methylenedioxy-1,4-dihydro-4-oxo-3-quinolinecarboxylic acid.

A. In vitro: minimum inhibitory concentration (MIC)

The compound was tested in a standard bacteriological tube dilution test for MIC for a variety of bacteria. Stock cultures of the bacteria listed in Table 1 were grown in bacterial culture media at 37° C. overnight and diluted in culture tubes to a previously determined concentration proper for the test. The compound was added to result in final concentrations of 10, 2, 0.4 and 0.8 $\mu$g/ml. These were incubated for 18 hours at 37° C. and then observed to determine if growth of bacteria had occurred. The lowest concentration of the compound that inhibited bacterial growth is the MIC. The data are shown in Table 1.

B. In vivo

1. *Escherichia coli* (mouse infections)

Female white mice weighing approximately 20 grams were infected by injecting a sufficient number of *E. coli* cells intraperitoneally to cause 85–100% fatalities within 3 days after infection. Groups of 12 such infected mice were dosed orally by intubation with the compound suspended in water to equal 40, 20, 10 and 5 mg/kg at the time of infection and again 4 hours after infection time. The mice were observed for 72 hours and the test then terminated. The dose effective to save 50% of the mice ($ED_{50}$) was calculated by the Reed-Muench method (Reed L. J. Muench, H. A Single Method of Estimating 50% Endpoints, Am. J. Hygiene 27, p. 493–497 (1938)). These data appear in Table 2.

2. *Staphylococcus aureus* (mouse infections)

The same methods as the previous test were used, except the compound concentrations were 400, 200, 100 and 50 mg/kg. The $ED_{50}$'s appear in Table 2.

C. General Pharmacology Screen

Method 17- to 24-hour fasted female white mice, 16–20 g. each, or rats, 70–90 g. each were dosed orally with test drug (or standard) at 0, 4, 12, 36, 108 or 324 mg./kg. Mice were observed at 0.5, 2, 5 and 24 hours after drug for number of survivors, and for signs of ataxia, vertical bar loss, hypo- or hyper-thermia, excitement and irritability upon handling and appetite loss (anorexia). Rats were observed similarly at 1, 2, 4, 6 and 24 hours after drug except that the anorexia test was not performed.

Ataxia—The mouse or rat was placed upright on the bench top facing away from the observer. Motor incoordination manifested by abnormal gait or lack of precision during purposive movements constituted ataxia. Mice which did not walk or run spontaneously were prodded gently.

Vertical Bar—The mouse or rat was swung by the tail with head pointing down to a 0.5″ diameter (1″ diameter for rats), 30.5 cm long vertical rod covered with adhesive tape. Inability to grip the rod with the front paws, sliding or failure to move after being prodded constituted vertical bar loss.

Body Temperature—The rectal temperatures of the mice and rats were taken using a KC-1 thermocouple probe. Temperatures more than 2 standard deviations below the mean temperature of vehicle-treated control animals constituted hypothermia, while temperature greater than 2 standard deviations above the mean were considered hyperthermic.

Excitement and Irritability—Increased spontaneous motor activity, running and jumping prior to handling were recorded as excitement. Upon handling, jumping, jerking, biting and squeaking were recorded as irritability.

Anorexia—At the end of the 0.5 hour testing period, each mouse was transferred to an individual, clear, Lucite® compartment (13.3 cm×12.7 cm×12.7 cm) with a 0.64 cm×0.64 cm wire mesh floor. Inside each compartment there was a section of a black Lucite® bar [13 cm×1.2 cm×1.2 cm] with ten spot depressions (0.8 cm diameter) each containing 0.05 ml. of 50% sweetened condensed milk. 30 Minutes later the number of milk spots consumed was counted. 5 Mice per drug dose can drink a maximum of 50 spots (2.5 ml. of milk). 15 or fewer spots consumed by 5 mice constituted anorexia.

Results -

An ED$_{50}$, the calculated dose at which 50% of the test animals would have responded was calculated for each of the described parameters for the compound of invention and the standard drugs; the ED$_{50}$'s are in Tables 3 and 4.

TABLE 1

In Vitro Activity of 1-difluoromethyl-6,7-methylenedioxy-1,4-dihydro-4-oxo-3-quinolinecarboxylic acid (DFMQ), oxolinic acid and nalidixic acid

| Test Organisms | Minimal Inhibitory Test Concns.* (µg/ml) | | |
|---|---|---|---|
| | DFMQ | Oxolinic Acid | Nalidixic Acid |
| Gram-Negative Bacteria: | | | |
| Sal. typhi (02A)** | 2 | 0.4 | 10 |
| Sal. typhi (02B) | 0.4 | 0.4 | 2 |
| Sal. typhosa (02D) | <0.08 | 0.4 | 2 |
| Sal. typhimurium (03A) | 0.4 | 0.4 | 2 |
| Sal. typhimurium (03C) | 0.4 | 0.4 | 2 |
| Sal. typhimurium (03K) | <0.08 | <0.08 | 2 |
| Sal. gallinarum (04C) | 2 | 2 | >10 |
| Sal. gallinarum (04D) | 0.4 | 0.4 | 10 |
| Sal. choleraesuis (18F) | <0.08 | <0.08 | 2 |
| Shig. dysenteriae (27A) | 0.4 | 0.4 | >10 |
| E. coli (06C) | 2 | 2 | >10 |
| E. coli (06I) | 10 | 10 | >10 |
| E. coli (06J) | 0.4 | 0.4 | 2 |
| E. coli (06K) | 0.4 | 0.4 | 10 |
| E. coli (06L) | 0.4 | 0.4 | 10 |
| E. coli (06M) | 0.4 | 0.4 | 10 |
| E. coli (06S) | 0.4 | 2 | 10 |
| E. coli (06V) | 0.4 | 0.4 | 2 |
| E. coli (06X) | 2 | 2 | 10 |
| E. coli (06-2B) | 2 | 2 | >10 |
| E. coli (06-2D) | 2 | 2 | 10 |
| E. coli (06-2F) | 0.4 | 0.4 | 2 |
| E. coli (06-2L) | 10 | 10 | >10 |
| E. coli (06-2M) | <0.08 | <0.08 | 2 |
| Pseud. aeruginosa (11B) | 10 | 2 | >10 |
| Pseud. aeruginosa (11C) | 2 | 2 | >10 |
| Pseud. aeruginosa (11D) | 10 | 10 | >10 |
| Pseud. aeruginosa (11G) | 10 | 10 | >10 |
| Pseud. aeruginosa (11I) | 2 | 2 | >10 |
| Pseud. aeruginosa (11J) | 10 | 2 | >10 |
| Proteus vulgaris (14P) | 2 | 2 | >10 |
| Proteus sp. | <0.08 | <0.08 | 2 |
| Kleb. aerobacter (20F) | 2 | >10 | >10 |
| Ser. marcascens (22) | 0.4 | 0.4 | 2 |
| Aero. cloacae (39A) | <0.08 | <0.08 | 2 |
| Gram-Positive Bacteria: | | | |
| Rac. subtilis (07A) | <0.08 | <0.08 | 0.4 |
| Staph. aureus (0SF) | 0.4 | 0.4 | 2 |
| Strep. pyogenes (10V) | <0.08 | <0.08 | 10 |

*brain-heart infusion broth, 20-hour incubation at 37° C.
**These numbers identify the particular type and source of organism.

TABLE 2

EFFECTS OF 1-DIFLUOROMETHYL-6,7-METHYLENE-DIOXY-1,4-DIHYDRO-4-OXO-3-QUINOLINECARBOXYLIC ACID IN MOUSE INFECTIONS OF ESCHERICHIA COLI AND STAPHYLOCOCCUS AUREUS

| ED$_{50}$[1] (mg/kg) | |
|---|---|
| Escherichia coli | Staphylococcus aureus |
| 9.9 | 149 |

[1]Reed Muench

TABLE 3

GENERAL PHARMACOLOGY OF 1-DIFLUOROMETHYL-6,7-METHYLENEDIOXY-1,4-DIHYDRO-4-OXO-3-QUINOLINECARBOXYLIC ACID (DMFQ), OXOLINIC ACID. AND NALIDIXIC ACID IN MICE

| Drug | Species | N | ED$_{50}$ Values | | | | | | | |
|---|---|---|---|---|---|---|---|---|---|---|
| | | | 24-Hour Mort. | Ataxia | Vert. Bar | Anorexia | Hypotherm. | Hypertherm. | Excitation | Irritability |
| DMFQ | Mouse | 15 | >450. | >450. | >450. | >450. | >450. | >450. | >450. | >450. |
| Oxolinic Acid | Mouse | 10 | >450. | 3.2 | 1.5 | 21. | >450. | >450. | 8. | 36. |
| Nalidixic Acid | Mouse | 10 | >450. | 150. | 187. | 180. | 187. | >450. | >450. | >450. |

TABLE 4

GENERAL PHARMACOLOGY OF 1-DIFLUOROMETHYL-6,7-METHYLENEDIOXY-1,4-DIHYDRO-4-OXO-3-QUINOLINECARBOXYLIC ACID (DMFQ), OXOLINIC ACID, AND NALIDIXIC ACID IN RATS

| Drug | Species | N | ED$_{50}$ Values | | | | | | | |
|---|---|---|---|---|---|---|---|---|---|---|
| | | | 24-Hour Mort. | Ataxia | Vert. Bar | Anorexia | Hypotherm. | Hypertherm. | Excitation | Irritability |
| DFMQ | Rat | 5 | >324. | >324. | >324. | — | >324. | >324. | >324. | >324. |
| Oxolinic Acid | Rat | 5 | >324. | 97. | 187. | — | >324. | 121. | 62. | >324. |
| Nalidixic Acid | Rat | 5 | >324. | 187. | 360. | — | >324. | >324. | >324. | >324. |

I claim:

1. A process for preparing a compound of the formula:

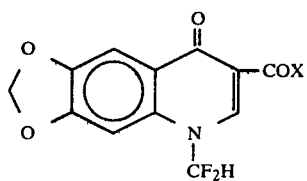

, wherein X=—OCH₃, —OCH₂H₅, —OC₃H₇ or —Cl, which comprises contacting a compound of the formula:

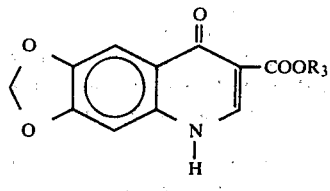

where
R₃=CH₃, C₂H₅, or C₃H₇; with the radical :CF₂ in an aprotic solvent; then optionally hydrolyzing in dilute acid and contacting with PCl₅.

2. The process of claim 1 wherein the :CF₂ radical is formed by pyrolysis of an alkaline metal salt of chlorodifluoroacetic acid.

3. The process of claim 1 wherein the :CF₂ radical is formed with chlorodifluoromethane in the presence of a base.

* * * * *